United States Patent [19]

Duckworth

[11] 4,382,958
[45] May 10, 1983

[54] SECONDARY AMINES AND COMPOSITIONS FOR TREATMENT OF HYPOGLYCAEMIA OR OBESITY

[75] Inventor: David M. Duckworth, Tadworth, England

[73] Assignee: Beecham Group Limited, England

[21] Appl. No.: 319,604

[22] Filed: Nov. 9, 1981

[30] Foreign Application Priority Data

Nov. 20, 1980 [GB] United Kingdom ............ 8037299

[51] Int. Cl.³ .................... A61K 31/135; C07C 87/28
[52] U.S. Cl. ................................. 424/330; 564/363
[58] Field of Search ............ 564/337, 363; 560/42; 562/451; 424/330

[56] References Cited

U.S. PATENT DOCUMENTS

| | | | |
|---|---|---|---|
| 3,983,164 | 9/1976 | Thorne et al. | 424/308 X |
| 4,072,760 | 2/1978 | Hedegaard | 562/451 X |
| 4,309,443 | 9/1980 | Smith et al. | 424/319 |

FOREIGN PATENT DOCUMENTS

| | | |
|---|---|---|
| 4835 | 10/1979 | European Pat. Off. . |
| 6735 | 1/1980 | European Pat. Off. . |
| 2034277 | 7/1970 | Fed. Rep. of Germany . |
| 2367487 | of 1978 | France . |
| 1513110 | 6/1978 | United Kingdom . |
| 2002765 | 2/1979 | United Kingdom . |

*Primary Examiner*—Bernard Helfin
*Attorney, Agent, or Firm*—Jacobs & Jacobs

[57] ABSTRACT

A compound of formula (I):

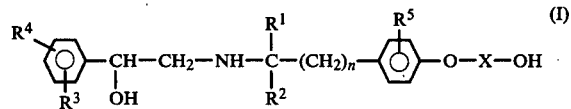

or a salt thereof; wherein $R^1$ is hydrogen, methyl or ethyl; $R^2$ is hydrogen, methyl or ethyl; $R^3$ is hydrogen, fluorine, chlorine, bromine or trifluoromethyl; each of $R^4$ and $R^5$ is hydrogen, fluorine, chlorine, bromine, $C_{1-6}$ alkyl or $C_{1-6}$ alkoxy; n is 1 or 2; and X is $C_{1-12}$ straight or branched alkylene, and salts thereof, are anti-obesity, hypoglycaemic, anti-inflammatory and platelet aggregation inhibiting agents.

8 Claims, No Drawings

SECONDARY AMINES AND COMPOSITIONS FOR TREATMENT OF HYPOGLYCAEMIA OR OBESITY

The present invention relates to derivatives of 2-phenylethanolamine which have anti-obesity and/or hypoglycaemic and/or anti-inflammatory and/or platelet aggregation inhibition activity, to processes for their production and to their use in medicine.

European patent application No. 79301197.4 (Beechams) discloses compounds of formula

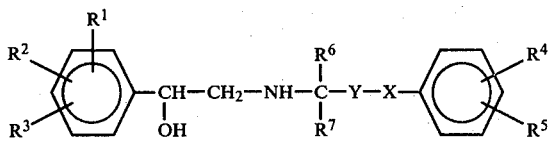

wherein
$R^1$ is hydrogen, fluorine, chlorine, hydroxyl, hydroxymethyl, methyl, methoxy, amino, formamido, acetamido, methylsulphonamido, nitro, benzyloxy, methylsulphonylmethyl, ureido, trifluoromethyl or p-methoxybenzylamino;
$R^2$ is hydrogen, fluorine, chlorine or hydroxyl;
$R^3$ is hydrogen, fluorine, chlorine or hydroxyl;
$R^4$ is a carboxylic acid group or a salt, ester or amide thereof;
$R^5$ is hydrogen, fluorine, chlorine, methyl, methoxy, hydroxyl, or a carboxylic acid group or a salt, ester or amide thereof,
$R^6$ is hydrogen, methyl, ethyl or propyl;
$R^7$ is hydrogen, methyl, ethyl or propyl;
X is oxygen or a bond; and
Y is $C_{1-6}$ alkylene or a bond,
which possess anti-obesity and/or hypoglycaemic activity.

It has now been discovered that a class of novel 2-phenylethanolamine derivatives have anti-obesity and/or hypoglycaemic and/or anti-inflammatory and/or platelet aggregation inhibition activity. These activities are coupled with low cardiac stimulant activity for particular members of the class.

Accordingly, the present invention provides a compound of formula (I):

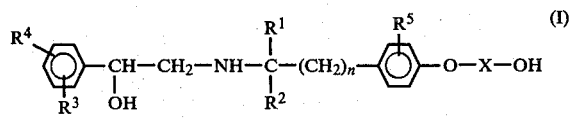

or a salt thereof; wherein $R^1$ is hydrogen, methyl or ethyl; $R^2$ is hydrogen, methyl or ethyl; $R^3$ is hydrogen, fluorine, chlorine, bromine or trifluoromethyl; each of $R^4$ and $R^5$ is hydrogen, fluorine, chlorine, bromine, $C_{1-6}$ alkyl or $C_{1-6}$ alkoxy; n is 1 or 2; and X is $C_{1-12}$ straight or branched alkylene.

Preferred compounds of formula (I) are those wherein each of $R^4$ and $R^5$ is hydrogen, and X is $C_{1-6}$ straight or branched alkylene. More preferably X is $C_{2-6}$ straight or branched alkylene.

Suitably, n is 1.

$R^3$ may be in any position on the aromatic ring, but is preferably in the meta-position.

Pharmaceutically acceptable salts of compounds of formula (I) include acid addition salts formed with a pharmaceutically acceptable acid such as hydrochloric acid, hydrobromic acid, orthophosphoric acid, sulphuric acid, methane sulphonic acid, toluenesulphonic acid, acetic acid, propionic acid, lactic acid, citric acid, fumaric acid, malic acid, succinic acid, salicylic acid or acetylsalicylic acid.

The salts of compounds of formula (I) need not be pharmaceutically acceptable as they are also useful in the preparation of other compounds of formula (I) and in the separation of stereoisomers of compounds of formula (I) when the salt ion is also optically active.

Compounds of formula (I) have at least one asymmetric carbon atom, ie the one bearing the hydroxyl and substituted phenyl groups, and, when $R^1$ and $R^2$ are different, the carbon atom bearing $R^1$ and $R^2$ is also asymmetric. The compounds may therefore exist in at least two and often four stereoisomeric forms. The present invention encompasses all stereoisomers of the compounds of formula (I) whether free from other stereoisomers or admixed with other stereoisomers in any proportion and thus includes, for instance, racemic mixtures of enantiomers.

Preferably, the carbon atom bearing the hydroxyl and substituted phenyl groups has the R configuration.

The most potent compounds of formula (I) are those wherein $R^1$ and $R^2$ are different and both asymmetric carbon atoms are in the R configuration.

The absolute configuration of any compound of formula (I) may be determined by conventional X-ray crystallographic techniques.

It is believed that, in the $^{13}C$ n.m.r. of compounds of formula (I) wherein one of $R^1$ and $R^2$ is hydrogen and the other is methyl, the diastereoisomer having the greater anti-obesity activity is that for which the signal of the methyl group carbon atom appears at higher field (the lower numerical value when expressed in ppm) in $d_6$DMSO solution. The paired resonances often appear at approximately 20 ppm (less active) and slightly below 20 ppm (more active) down field from tetramethylsilane. Other paired resonances can occur for the carbon atoms attached directly to the nitrogen atom and the carbon which carries the hydroxyl and phenyl groups. Again the paired resonances of the more active diastereoisomer of the investigated compounds appear at the higher field position.

The present invention provides a process for producing a compound of formula (I) or a salt thereof, which process comprises reducing an oxo-group and/or a double bond and/or an ester group of a compound of formula (II):

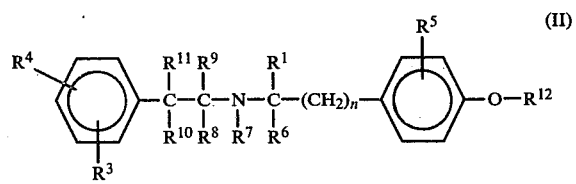

wherein
$R^1$, $R^3$, $R^4$, $R^5$ and n are as defined in relation to formula (I);
$R^{12}$ is a group X—OH as defined in relation to formula (I), or a group

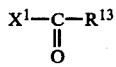

wherein $X^1$ is a $C_{1-11}$ straight or branched chain alkylene or alkenylene and $R^{13}$ is an ester forming radical;

$R^6$ is a group $R^2$ as defined in relation to formula (I) or together with $R^7$ forms a bond;

$R^7$ is hydrogen or together with $R^6$ or $R^8$ forms a bond;

$R^8$ is hydrogen or together with $R^9$ forms an oxo-group or together with $R^7$ forms a bond;

$R^9$ is hydrogen or together with $R^8$ forms an oxo-group;

$R^{10}$ is hydrogen or hydroxyl or together with $R^{11}$ forms an oxo-group;

$R^{11}$ is hydrogen or together with $R^{10}$ forms an oxo-group, provided that there is no more than one oxo-group and no more than one bond represented by any of $R^6$ to $R^{11}$, and optionally thereafter forming a salt of the compound of formula (I) so formed.

Suitably $R^{13}$ is a $C_{1-6}$ alkoxy group, such as methoxy.

Where there are two or more reducible moieties in the compound of formula (I) these may be reduced separately in any order or simultaneously. In particular, when $R^{12}$ is a group

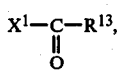

this may be reduced before or after a reducible moiety represented by any of $R^6$ to $R^{11}$ or conveniently, such a group $R^{12}$ may be reduced simultaneously with reducible moieties represented by $R^6$ to $R^{11}$.

When $R^{12}$ is a group

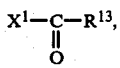

this is reduced to a group X—OH wherein there is one more carbon atom in the alkylene group X than in the starting material alkylene group $X^1$.

The aforementioned reductions may be effected by conventional chemical or catalytic methods, such as chemical reduction using lithium aluminium hydride, sodium cyanoborohydride or sodium borohydride or by catalytic hydrogenation using catalysts such as palladium on charcoal, or platinum, for instance, as platinum oxide.

Reduction by sodium borohydride is conveniently effected in a lower alkanolic solvent such as methanol. The reaction is generally carried out at from 0°–20° C.

Reduction by lithium aluminium hydride is conveniently effected in a dry, ether solvent such as diethyl ether or tetrahydrofuran at ambient or elevated temperature.

Catalytic reduction is conveniently effected in a conventional hydrogenation solvent such as a lower alkanol, for instance ethanol. The hydrogenation is generally carried out under hydrogen gas at about 1 atmosphere pressure to about 10 atmosphere pressure and at ambient or elevated temperature.

In particular aspects, the present invention provides processes for producing compounds of formula (I) by reducing a compound of formula (IIA):

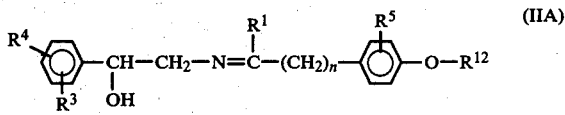

or reducing a compound of formula (IIB):

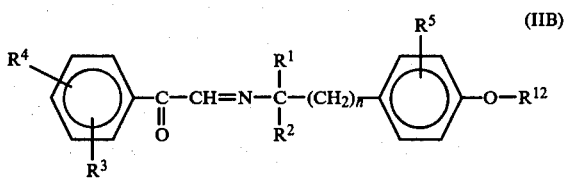

or reducing a compound of formula (IIC):

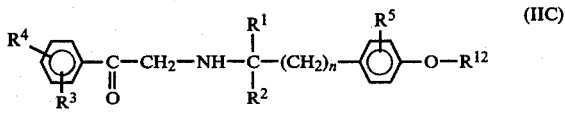

or the N-benzyl derivative thereof, or reducing a compound of formula (IID):

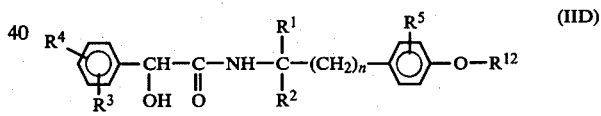

or reducing a compound of formula (IIE):

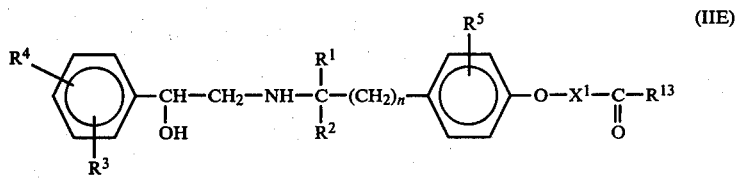

wherein $R^1$, $R^2$, $R^3$, $R^4$, $R^5$ and n, are as defined in relation to formula (I) and $R^{12}$, $R^{13}$ and $X^1$ are as defined in relation to formula (II).

The present invention also provides another process for producing a compound of formula (I) or a salt thereof, which process comprises reacting a compound of formula (III):

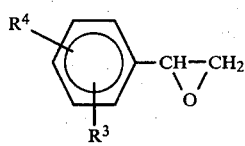 (III)

with a compound of formula (IV):

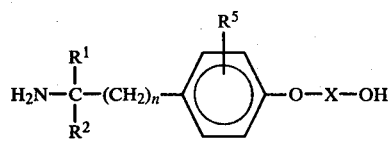 (IV)

wherein $R^1$, $R^2$, $R^3$, $R^4$, $R^5$, X and n are as defined in relation to formula (I), and optionally thereafter forming a salt of the compound of formula (I) so formed.

This reaction is conveniently effected in a solvent such as a lower alkanol, preferably ethanol.

A particularly preferred process for producing compounds of formula (I) comprises the reduction of a compound of formula (IIA), especially using sodium borohydride in methanol at ambient temperature.

A further preferred process for producing compounds of formula (I) comprises the reduction of a compound of formula (IIE), especially using sodium borohydride in methanol or lithium aluminium hydride in dry diethyl ether or tetrahydrofuran under reflux.

The salts of compounds of formula (I) may be produced by treating the compound of formula (I) with the appropriate acid.

Compounds of formula (I) and salts thereof, produced by the above processes, may be recovered by conventional methods.

Compounds of formula (I) having a single asymmetric carbon atom may, if desired, be separated into individual enantiomers by conventional means, for example by the use of an optically active acid as a resolving agent. Those compounds of formula (I) having two asymmetric carbon atoms may be separated into diastereoisomeric pairs of enantiomers by, for example, fractional crystallisation from a suitable solvent such as ethyl acetate. The pair of enantiomers thus obtained may be separated into individual stereoisomers by conventional means such as by the use of an optically active acid as a resolving agent.

Suitable optically active acids which may be used as resolving agents are described in "Topics in Stereochemistry" Vol 6, Wiley Interscience, 1971, Allinger, N. L. and Eliel, W. L. Eds.

Alternatively any enantiomer of a compound of formula (I) may be obtained by stereospecific synthesis using optically pure starting materials of known configuration.

Compounds of formula (II) may be produced by reacting a compound of formula (V):

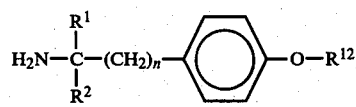 (V)

wherein $R^1$, $R^2$ and n are as defined in relation to formula (I), and $R^{12}$ is as defined in relation to formula (II), with a compound of formula (VI):

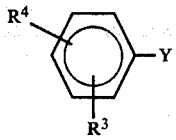 (VI)

wherein $R^3$ and $R^4$ are as defined in relation to formula (I) and Y is a reactive moiety which is capable of reacting with the amine of formula (V) thus forming a compound of formula (II). Typical examples of compounds of formula (VI) are:

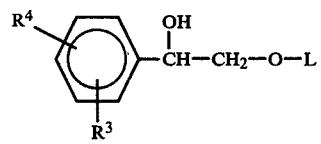 (VIE)

wherein O—L is a leaving group, preferably tosyloxy

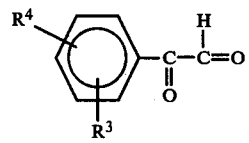 (VIA)

or its hydrate or hemi-acetal of a lower alkanol;

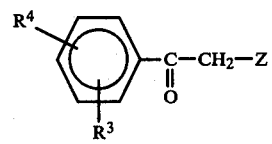 (VIB)

wherein Z is a halogen atom, preferably bromine;

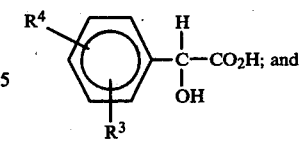 (VIC)

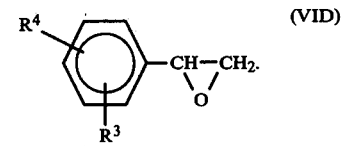 (VID)

Conventional conditions suitable for use with the particular compound of formula (VI) may be used for this reaction. Thus the reaction of a compound of formula (VIA) with a compound of formula (V) is conveniently conducted at elevated temperature under conditions resulting in the removal of the water formed during the reaction. A particularly suitable method is to perform the reaction in a solvent, such as benzene, under reflux and azeotropically to remove the water using a Dean and Stark trap.

The reaction of a compound of formula (VIB) with a compound of formula (V) is conveniently conducted in a polar organic solvent such as acetonitrile or butanone, at an elevated temperature, for instance under reflux.

The reaction of a compound of formula (VIC) with a compound of formula (V) is conveniently conducted under standard peptide formation reaction conditions.

The reaction of a compound of formula (VID) with a compound of formula (V) is conveniently conducted in a solvent such as a lower alkanol, preferably ethanol.

By using single enantiomers of a compound of formula (V) and a compound of formula (VI) such as the compounds (VIC) or (VID) a stereospecific synthesis of a compound of formula (II) is achieved. This may then be reduced to a compound of formula (I) without altering the configuration of the two asymmetric carbon atoms. Thus, for example, a compound of formula (V) with the R absolute configuration and a compound of formula (VID) with the R absolute configuration would afford a compound of formula (I) with the RR absolute configuration.

In a modification of the above process for producing compounds of formula (II), the N-benzyl derivative of a compound of formula (V) may be reacted with a compound of formula (VIB). In this case the N-benzyl derivative of formula (II) is produced and this may be reduced to a compound of formula (I) using a catalytic hydrogenation reaction, especially using palladium on charcoal as catalyst, Certain compounds of formula (II) may also be produced by reacting a compound of formula (VII):

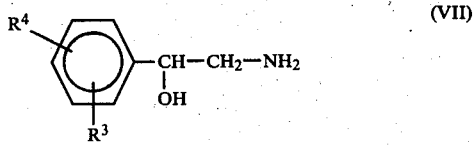

with a compound of the formula (VIII):

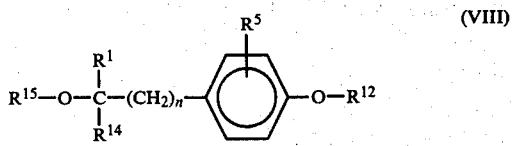

wherein $R^1$, $R^3$, $R^4$, $R^5$ and n are as defined in relation to formula (I) and $R^{12}$ is as defined in relation to formula (II), $R^{14}$ is a group $R^2$ or together with $R^{15}$ forms a bond and $R^{15}$ is a group L such that O-L is a leaving group, preferably tosyloxy, or together with $R^{14}$ forms a bond.

The reaction of a compound of formula (VII) with a ketone of formula (VIII) is conveniently effected under conditions which result in the removal of water formed during the reaction. A particularly suitable method is to perform the reaction in a solvent, such as benzene, under reflux and azeotropically to remove the water using a Dean and Stark trap.

The reaction of a compound of formula (VII) with a compound of formula (VIII) wherein $R^{15}$ is a group L is conveniently effected in a solvent such as dimethyl sulphonide at elevated temperature, preferably at about 50° C. for about two to three days.

It is often convenient to prepare the compound of formula (II) and reduce it, in situ, to the desired compound of formula (I) without isolation of the compound of formula (II).

A compound of formula (I) or a pharmaceutically acceptable salt thereof (hereinafter "the drug") may be administered as the pure drug, however, it is preferred that the drug be administered as a pharmaceutical composition also comprising a pharmaceutically acceptable carrier.

Accordingly, the present invention also provides a pharmaceutical composition comprising a compound of formula (I) or a pharmaceutically acceptable salt thereof with a pharmaceutically acceptable carrier therefor.

As used herein the terms "pharmaceutical composition" and "pharmaceutically acceptable" embrace compositions and ingredients for both human and veterinary use.

Usually the compositions of the present invention will be adapted for oral administration although compositions for administration by other routes, such as by injection are also envisaged.

Particularly suitable compositions for oral administration are unit dosage forms such as tablets and capsules. Other fixed-unit dosage forms, such as powders presented in sachets, may also be used.

In accordance with conventional pharmaceutical practice the carrier may comprise a diluent, binder, filler, disintegrant, wetting agent, lubricant, colourant, flavourant, or the like.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.1 to 500 mg of the drug, more usually 0.1 to 250 mg and favourably 0.1 to 100 mg.

The present invention further provides a method for treating obesity in human or non-human animals, which method comprises administering an effective, non-toxic amount of a compound of formula (I) or a pharmaceutically acceptable salt thereof to the obese animal.

Conveniently, the drug may be administered as a pharmaceutical composition as hereinbefore defined, and this forms a particular aspect of the present invention.

In treating obese humans the drug may be taken in doses, such as those described above, one to six times a day in a manner such that the total daily dose for a 70 kg adult will generally be about 0.1 to 1000 mg, and more usually about 1 to 500 mg.

In treating obese non-human animals, especially domestic mammals such as dogs, the drug may be administered by mouth, usually once or twice a day and at about 0.025 mg/kg to 5.0 mg/kg, for example 0.1 mg/kg to 2 mg/kg.

The present invention further provides a method for treating hyperglycaemia in humans which method comprises administering an effective, non-toxic amount of a compound of formula (I) or a pharmaceutically acceptable salt thereof to hyperglycaemic humans.

The drug may be taken in doses such as those described above for treating obese humans.

The present invention also provides a method for the treatment or prophylaxis of inflammation in humans, which comprises topically administering an effective non-toxic amount of a compound of formula (I) or a pharmaceutically acceptable salt thereof to humans suffering inflammation.

The present invention further provides a method of inhibiting platelet aggregation in humans, which comprises administering to the sufferer an effective non-toxic amount of a compound of formula (I) or a pharmaceutically acceptable salt thereof.

The invention will now be illustrated with reference to the following Examples, which are not intended to limit the scope in any way. The preparation of intermediates is described in the following Descriptions.

All temperatures are in °C.

EXAMPLE 1

N-[2-(4-(2-Hydroxyethoxy)phenyl)-1-methylethyl]-2-hydroxy-2-(2-fluorophenyl)ethanamine

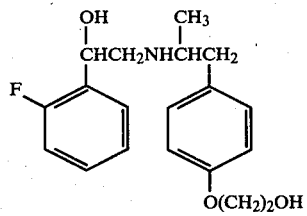

A mixture of 1-(4-carbomethoxymethoxyphenyl)propan-2-one (2.22 g) and 2-hydroxy-2-(2-fluorophenyl)ethanamine (1.55 g) in benzene (100 ml) was boiled under reflux with azeotropic removal of water using a Dean and Stark trap, for 2 hours. The solution was cooled, evaporated to dryness, the residue dissolved in methanol and sodium borohydride (500 mg) added. After 30 minutes, the methanol was evaporated and the residue partitioned between ethyl acetate and water. The organic layer was dried (magnesium sulphate) and evaporated to leave an oil which was chromatographed on silica gel 60 eluting with 2% methanol/chloroform. N-[2-(4-(2-hydroxyethoxy)phenyl-1-methylethyl]-2-hydroxy-2-(2-fluorophenyl)ethanamine (300 mg) crystallised from hexane, m.p. 80°-95°, as a 55:45 mixture of diastereoisomers.

'Hnmr

τ(CDCl₃) 8.95 (3H, d, J=6 Hz), 6.75-8.2 (5H, m+3H replaceable by D₂O), 5.9-6.2 (4H, m) 5.1 (1H, m), 2.3-3.3 (8H, m).

EXAMPLE 2

N-[2-(4-Hydroxybutoxy)phenyl)-1-methylethyl]-2-hydroxy-2-(3-trifluoromethylphenyl)ethanamine

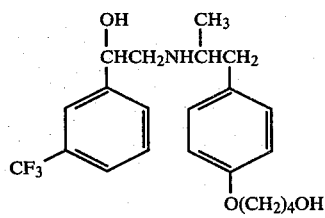

To a slurry of lithium aluminium hydride (200 mg) in dry tetrahydrofuran (20 ml) was added dropwise, with stirring, a solution of N-[2-(4-(3-carbomethoxypropoxy)phenyl)-1-methylethyl]-2-hydroxy-2-(3-trifluoromethylphenyl)ethanamine (800 mg) in dry tetrahydrofuran (30 ml). The mixture was stirred and heated under reflux for 2 hours after which time it was cooled in ice. Water (0.2 ml), 2 M sodium hydroxide (0.2 ml) and water (1 ml) were successively added, the resulting mixture filtered, the tetrahydrofuran dried (magnesium sulphate) and evaporated to leave an oil. Crystallisation from hexane gave N-[2-(4-(4-hydroxybutoxy)phenyl)-1-methylethyl]-2-hydroxy-2-(3-trifluoromethylphenyl)ethanamine (450 mg) m.p. 69°-76° as a 45:55 mixture of diastereoisomers.

'Hnmr

τ(CDCl₃) 8.9 (3H, d, J=6 Hz), 7.6-8.5 (2H, m, +3H-replaceable by D₂O), 6.9-7.5 (7H, m), 6.3 (2H, t, J=6 Hz), 6.0 (2H, t, J=6 Hz), 5.4 (1H, m), 3.2 (2H, dd, J=8 Hz, J=2 Hz), 2.9 (2H, dd, J=8 Hz) J=2 Hz), 2.3-2.5 (4H,m).

EXAMPLE 3

N-[2-(4-(2-Hydroxyethoxy)-phenyl)-1-methylethyl]-2-hydroxy-2-(3-trifluoromethylphenyl)ethanamine

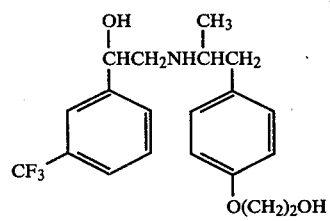

To a solution of N-[2-(4-carbomethoxymethoxyphenyl)-1-methylethyl]-2-hydroxy-2-(3-trifluoromethylphenyl)ethanamine (1.0 g) in absolute methanol (50 ml) at ambient temperature was added sodium borohydride (1.0 g) in small portions over a period of 30 minutes with vigorous stirring. The mixture was boiled under reflux for 2 hours, cooled to room temperature and the solvent removed under vacuum. The residue was partitioned between water and dichloromethane, the organic layer dried (MgSO₄) and evaporated to yield a brown oil (0.81 g) which on chromatography on silica-gel in dichloromethane/methanol mixtures gave a waxy solid. Recrystallisation from 50% 40.60 petroleum ether—ether gave a white solid (0.25 g) m.p. 91°-97° C., as a 58:42 mixture of diastereoisomers.

'Hnmr

τ(CDCl₃): 8.95 (3H, d, J=6 Hz), 6.7-7.7 (5H, m, +3H broad, replaceable by D₂O), 6.05 (4H, s), 5.40 (1H, m), 3.20 (2H, d, J=8 Hz), 2.95 (2H, d, J=8 Hz), 2.3-2.7 (4H, m).

EXAMPLE 4

N-[2-(4-(3-Hydroxypropoxy)phenyl)-1-methylethyl]-2-hydroxy-2-(3-trifluoromethylphenyl)-ethanamine

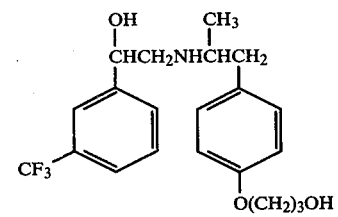

A mixture of 1-[4-(3-hydroxypropoxy)phenyl]-propan-2-one (1.8 g) and 2-hydroxy-2-(3-trifluoromethylphenyl)ethanamine (1.8 g) were mixed in dry benzene (80 ml) and boiled under reflux in a Dean and Stark apparatus until water evolution was complete. The solvent was evaporated, the residue dissolved in methanol, platinum oxide (50 mg) added and the imine reduced in the presence of hydrogen at atmospheric pressure. When hydrogen uptake ceased the catalyst was removed by filtration and the solvent evaporated. The residue was chromatographed on silica-gel in 4% methanol-dichloromethane to give the title compound (0.94 g) as a colourless oil. Crystallisation from ether-hexane gave a white solid, mp 97°–103°, as a 74:26 mixture of diastereoisomers.

τ(CDCl$_3$) 8.9 (3H, d, J=6 Hz), 8.0 (2H, complex), 6.9–7.5 (8H, complex, 3H exchangeable with D$_2$O), 5.9–6.5 (4H, complex), 5.4 (1H, complex), 3.2 (2H, d, J=8 Hz), 2.9 (2H, d, J=8 Hz), 2.45 (4H, complex).

EXAMPLE 5

N-[2-(4-(6-Hydroxyhexyloxy)phenyl)-1-methylethyl]-2-hydroxy-2-(3-trifluoromethylphenyl)-ethanamine

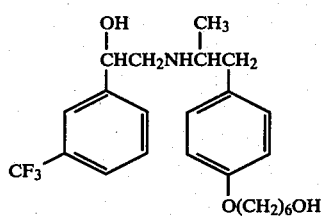

The title compound was prepared as in Example 4, using 1-[4-(6-hydroxyhexyloxy)phenyl]-propan-2-one (3.3 g) to give 1.1 g of white crystals (hexane-ether), mp 68°–73° C. as a 58:42 mixture of diastereoisomers.

τ(CDCl$_3$) 8.9 (3H, d, J=6 Hz), 8.0–8.7 (8H, complex), 6.9–7.7 (8H, complex, 3H exchangeable with D$_2$O), 6.4 (2H, triplet), 6.1 (2H, triplet), 5.3 (1H, complex), 3.25 (2H, d, J=8 Hz), 2.95 (2H, d, J=8 Hz), 2.5 (4H, complex).

EXAMPLE 6

N-[2-(4-(11-Hydroxyundecyloxy)phenyl)1-methylethyl]-2-hydroxy-2-(3-trifluoromethylphenyl)-ethanamine

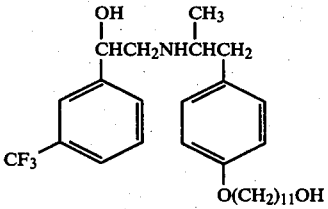

The compound was prepared as in Example 4, from 1-[4-(11-hydroxyundecyloxy)phenyl]propan-2-one (7.3 g) and 2-hydroxy-2-(3-trifluoromethylphenyl)-ethanamine (4.7 g) and purified by chromatography on silica gel in 5% methanol dichloromethane, mp 45°–50° C. as a 50:50 mixture of diastereoisomers.

τ(CDCl$_3$) 8.9 (3H, d, J=6 Hz), 8.1–8.85 (18H, complex), 7.7 (3H, broad singlet, exchangeable with D$_2$O), 6.9–7.6 (5H, complex), 6.4 (2H, t), 6.15 (2H, t), 5.3 (1H, complex), 3.2 (2H, d, J=8 Hz), 2.9 (2H, d, J=8 Hz), 2.4 (4H, complex).

EXAMPLE 7

N-[2-(4-(1,1-Dimethyl-2-hydroxyethoxy)phenyl)-1-methylethyl]-2-hydroxy-2-(3-trifluoromethylphenyl)-ethanamine

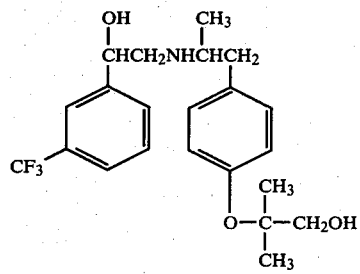

A mixture of 1-(4-αα-dimethylcarbomethoxymethoxyphenyl)propan-2-one (2.0 g) and 2-hydroxy-2-(3-trifluoromethylphenyl)ethanamine (1.66 g) in dry benzene was boiled under reflux in a Dean and Stark apparatus until water evolution was complete. The solvent was removed, the residue dissolved in methanol (80 ml) and treated portionwise with sodium borohydride (4.0 g) at ambient temperature. After stirring 1 hour at ambient temperature water (150 ml) was added, the mixture was extracted with dichloromethane, the extracts dried (MgSO$_4$) and the solvent removed under vacuum. Chromatography on silica gel in 4% methanol dichloromethane gave the title compound as a colourless oil.

τ(CDCl$_3$) 8.9 (3H, d, J=6 Hz), 8.7 (6H, s), 7.0–7.5 (8H, complex, 3H exchangeable with D$_2$O), 6.4 (2H, s), 5.35 (1H, m), 3.0 (4H, complex), 2.4 (4H, complex).

The product in ether was treated with a solution of hydrogen chloride in ether and after evaporation of the solvent and crystallisation of the residue from ethylacetate-ether, the title compound was obtained as its hydrochloride salt, mp 166°–8° C. as a 64:36 mixture of diastereoisomers.

EXAMPLE 8

N-[2-(4-(2-Hydroxyethoxy)phenyl)-1-methylethyl]-2-hydroxy-2-(3-fluoro-4-methoxyphenyl)-ethanamine

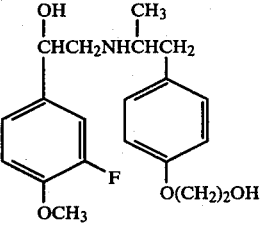

The compound was prepared as in Example 7, from 1-[4-(2-hydroxyethoxy)phenyl]propan-2-one (3.9 g) and 2-hydroxy-2-(3-fluoro-4-methoxyphenyl)-ethanamine (3.75 g) and crystallised from ether-hexane, mp 112°–115° C. as a 82:18 mixture of diastereoisomers.

τ(CDCl$_3$+DMSO-d$_6$) 8.9 (3H, d, J=6 Hz), 6.9–7.4 (4H, complex), 5.85–6.8 (11H, complex, 3H exchangeable with D$_2$O), 5.4 (1H, complex), 2.7–3.3 (7H, complex).

EXAMPLE 9

N-[3-[4-(2-Hydroxyethoxy)phenyl]-1,1-dimethyl-propyl]-2-hydroxy-2-phenylethanamine

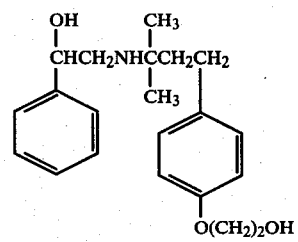

A solution of phenyl glyoxal monohydrate (3.6 g) and 3-[4-(2-hydroxyethoxy)phenyl]-1,1-dimethylpropylamine (5 g) in benzene (100 ml) was heated under reflux with removal of water by a Dean and Stark trap. When water removal was complete, the benzene was evaporated under reduced pressure, the residue dissolved in methanol and sodium borohydride (2 g) added. The solution was stirred at ice-water temperature for 15 minutes, the methanol evaporated and the residue portioned between ethyl acetate and water. The organic layer was dried MgSO$_4$ and evaporated to give a solid (6 g) which was purified on a silica gel column eluting with 4% methanol in chloroform. The product (2.8 g) was crystallised from dichloromethane, mp 118°–120° C.

τ(DMSO-d$_6$) 8.95 (6H, s), 8.3–8.7 (2H, m), 7.3–7.8 (4H, m), 6.2–6.4 (2H, m), 6.0–6.2 (2H, m), 5.5 (1H, m), 5.2 (3H, bs, replaceable by D$_2$O), 3.2 (2H, d, J=8 Hz), 2.9 (2H, d, J=8 Hz), 2.6 (4H, m).

EXAMPLE 10

N-[3-(4-(2-Hydroxyethoxy)phenyl)-1-methylpropyl]-2-hydroxy-2-(3-chlorophenyl)ethanamine

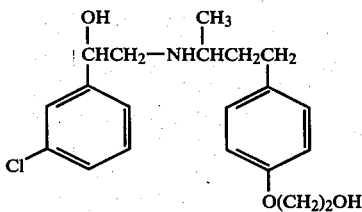

A mixture of 2-hydroxy-2(3-chlorophenyl)ethanamine (2.87 g) and 4-[4-(2-hydroxyethoxy)phenyl]butan-2-one (3.48 g) in benzene (250 ml) was treated under reflux in a Dean and Stark apparatus until water evolution was complete. The solvent was evaporated, the residue dissolved in methanol (200 ml) and cooled in ice. Sodium borohydride (5.3 g) was added in portions over 30 minutes. After a further hour at ambient temperature, the solvent was evaporated and the residue partitioned between water and ethyl acetate. The ethyl acetate layer was dried (MgSO$_4$) and evaporated to give an oil. Chromatography on silica gel in 5% methanol in dichloromethane gave the title compound as a white solid, mp 103°–5° C., as a 39:61 mixture of diastereoisomers.

τ(DMSO-d$_6$) 9.0 (3H, d), 8.2–8.7 (2H), 7.1–7.7 (5H, after D$_2$O exchange), 6.2–6.4 (2H, m), 6.0–6.2 (2H, m), 5.4 (1H, dd), 3.1 (2H, d), 2.9 (2H, d), 2.5–2.8 (4H, complex).

EXAMPLE 11

N-[2-{4-(2-Hydroxyethoxy)-3-methylphenyl}-1-methylethyl]-2-hydroxy-2-(3-trifluoromethylphenyl)ethanamine

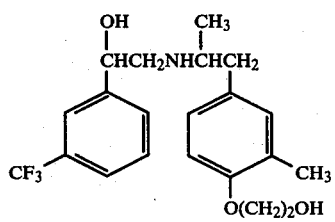

The title compound was prepared from N-[2-(4-carbomethoxymethoxy-3-methylphenyl)-1-methylethyl]-2-hydroxy-2-(3-trifluoromethylphenyl)ethanamine by an analogous procedure to that described in Example 2. Crystallisation of the product from ether-hexane gave the title compound as a white solid, mp 73°–9° C., of analytical purity.

τ(CDCl$_3$) 8.95 (3H, d), 6.9–7.9 (11H, complex w. singlet at 7.8), 5.8–6.15 (4H, m), 5.35 (1H, dd), 2.95–3.3 (3H, complex), 2.3–2.65 (4H, complex).

EXAMPLE 12

N-[2-(4-(2-Hydroxyethoxy)-phenyl)-1-methylethyl]-2-hydroxy-2-(3-chlorophenyl)ethanamine

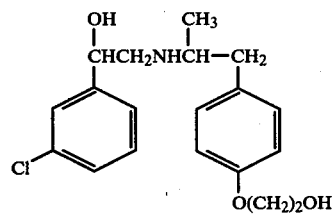

Starting from 2-hydroxy-2-(3-chlorophenyl)ethanamine (3.27 g) and 2-(4-(2-hydroxyethoxy)phenyl)propanone (3.46 g), the title compound (2.1 g) was prepared as in Example 4 as a colourless oil.

$^1$H nmr τ(CDCl$_3$) 8.9 (3H, d, J=6 Hz), 6.85–7.7 (5H, m), 6.5 (3H, broad s, replaceable by D$_2$O), 5.9–6.1 (4H, m), 5.25 (1H, m), 3.2 (2H, d, J=8 Hz), 2.95 (2H, d, J=8 Hz), 2.8 (4H, m).

EXAMPLE 13

N-[2-{4-(4-Hydroxybutoxy)phenyl}-1-(R)-1-methylethyl]-2-(R)-2-hydroxy-2-(3-trifluoromethylphenyl)ethanamine

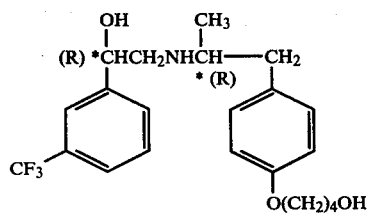

A solution of N[2-{4-(3-carbomethoxypropoxy)phenyl}-1-(R)-1-methylethyl]-2-(R)-2-hydroxy-1-oxo-2-(3-trifluoromethylphenyl)ethanamine (2.35 g) in dry tetrahydrofuran (30 ml) was added slowly to a refluxing suspension of lithium aluminium hydride (3.26 g) in dry tetrahydrofuran and then heated under reflux overnight. After careful addition of water (3.5 ml), 10% aqueous sodium hydroxide (4 ml) and water (8 ml), filtration and evaporation of the filtrate to dryness gave the crude product. Column chromatography on silica gel using 3% methanol in chloroform as eluent gave the title compound, mp 67°–70° (ethyl acetate-hexane), $[\alpha]_D^{25}$ methanol-29.7, (96% enantiomeric purity by g.c.).

$\tau$(CDCl$_3$) 8.95 (3H, d), 6.9–8.4 (12H, complex), 6.25 (2H,t), 6.05 (2H, t), 5.4 (1H, dd), 2.2–3.3 (8H, complex).

EXAMPLE 14

N-[3-(4-(2-Hydroxyethoxyphenyl)propyl)]-2-hydroxy-2-(3-chlorophenyl)-ethanamine To a solution of 2-hydroxy-2-(3-chlorophenyl)-ethanamine (3.7 g) in dry dimethylsulphoxide (50 ml) containing triethylamine (5 ml) was added 1-(4-carbomethoxymethoxyphenyl)-3-(4-methylphenylsulphonyloxy)-propane (7.4 g) and the mixture was stirred at 60° C. for 24 hours with exclusion of moisture. The solution was cooled, added to water (150 ml), extracted with ether (2×100 ml) and the organic extracts were dried (MgSO$_4$) and the solvent evaporated to give an oil.

N-[3-(4-(carbomethoxymethoxyphenyl)propyl)]-2-hydroxy-2-(3-chlorophenyl)-ethanamine (2.1 g) was obtained pure by chromatography of this oil on silica-gel in 5% methanol-dichloromethane. This product in methanol (100 ml) was treated portionwise with sodium borohydride (2.0 g) at ambient temperature. On completion of the addition the solution was stirred for a further hour at ambient temperature and water (250 ml) was added. The aqueous mixture was extracted with dichloromethane, the organic extracts dried (MgSO$_4$) and evaporated and the solid residue crystallised from methanol-dichloromethane to give the title compound Mp 127°–9° C.

$\tau$[(CD$_3$)$_2$SO] 8.32 (2H, m), 7.15–7.7 (6H, m) 6.3 (2H,t), 6.05 (2H,t) 5.4 (1H,t), 5.8–9.2 (1H, broad s, exchanges with D$_2$O) 5.0–5.4 (1H, broad s, exchanges with D$_2$O) 4.4–4.9 (1H, broad s, exchanges with D$_2$O) 3.2 (2H, d, J=8 Hz); 2.8 (2H, d, J=8 Hz) 2.6 (4H, complex).

Description 1

N-[2-(4-(3-Carbomethoxyprop-2-eneoxy)phenyl)-1-methylethyl]-2-hydroxy-2-(3-trifluoromethyl)ethanamine A mixture of 1-(4-(3-carbomethoxyprop-2-eneoxy)-phenyl)propan-2-one (2.12 g) and 2-hydroxy-2-(3-trifluoromethylphenyl)ethanamine (1.75 g) in benzene (100 ml) was boiled under reflux for two hours with azeotropic removal of water using a Dean and Stark trap. The solution was evaporated, the residue dissolved in methanol (50 ml), cooled in ice and sodium borohydride (500 mg) added. After 15 minutes the methanol was evaporated and the residue partitioned between water and ethyl acetate. The ethyl acetate layer was dried (magnesium sulphate) and evaporated to give a pale brown solid (3.5 g), which was chromatographed on silica gel 60 eluting with 2% methanol/chloroform to give N-[2-(4-(3-carbomethoxyprop-2-eneoxy)-phenyl)-1-methylethyl]-2-hydroxy-2-(3-trifluoromethyl)ethanamine as a cream solid (3 g), M.P. 65°–85° as a 50:50 mixture of diastereoisomers.

'Hnmr $\tau$(CDCl$_3$) 9.1 (3H, d, J=6 Hz), 7.0–7.7 (5H, m, +1H replaceable by D$_2$O), 6.3 (3H, s), 5.1–5.4 (3H, m), 4.4–4.8 (1H, broad, replaceable by D$_2$O), 3.85 (dt, 1H, J=16 Hz, J=2 Hz), 2.7–3.3 (5H, m), 2.2–2.55 (4H, m).

Description 2

N-[2-(4-(3-Carbomethoxypropoxy)phenyl)-1-methylethyl]-2-hydroxy-2-(3-trifluoromethylphenyl)ethanamine To a solution of N-[2-(4-(3-carbomethoxyprop-2-eneoxy)phenyl)-1-methylethyl]-2-hydroxy-2-(3-trifluoromethylphenyl)ethanamine (1.5 g) in absolute ethanol (50 ml) was added 10% Pd/C (200 mg) and the mixture hydrogenated at ambient temperature and atmospheric pressure until hydrogen uptake had ceased, (approximately 30 minutes). The mixture was filtered and the ethanol evaporated to leave N-[2-(4-(3-carbomethoxypropoxy)phenyl)-1-methylethyl]-2-hydroxy-2-(3-trifluoromethylphenyl)ethanamine as a light yellow oil which crystallised from hexane (1,0 g) m.p. 50°–60°.

'Hnmr $\tau$(CDCl$_3$) 8.95 (3H, d, J=6 Hz), 7.9 (2H, q, J=6 Hz), 6.5–7.6 (7H, m,+2H replaceable by D$_2$O), 6.3 (3H, s), 6.0 (2H, t, J=6 Hz), 5.4 (1H, m), 3.2 (2H, dd, J=8 Hz, J=2 Hz), 2.9 (2H, dd, J=8 Hz, J=2 Hz), 2.3–2.5 (4H, m).

Description 3

1-[4-(3-Hydroxypropyloxy)phenyl]propan-2-one 1-(4-Hydroxyphenyl)propan-2-one ethylene ketal (3.88 g) was added to a solution of sodium hydroxide (1.5 g) in water (30 ml) and the mixture was stirred at room temperature for 30 minutes. 1-Bromo-3-hydroxy-propane (2.98 g) was added and the mixture was boiled under reflux with stirring for 1½ hours. After cooling water (50 ml) was added, the mixture was extracted with ether, the extracts dried (MgSO$_4$) and evaporated to give the title compound (3.94 g) as its ethylene ketal.

$\tau$(CDCl$_3$) 8.7 (3H, s), 7.5–8.2 (3H, complex, 1H exchangeable with D$_2$O), 7.2 (2H, s), 5.8–6.6 (8H, complex), 3.25 (2H, d, J=8 Hz), 2.8 (2H, d, J=8 Hz).

The ketal was dissolved in methanol (50 ml), 2 N hydrochloric acid (30 ml) was added and the solution was allowed to stand at room temperature for 2 hours. Water (100 ml) was added, the solution extracted with ether, the extracts dried (MgSO$_4$) and evaporated to give the title compound (1.8 g) as an oil which was used without further purification.

Description 4

1-[4-(6-Hydroxyhexyloxy)phenyl]propan-2-one

The title compound was prepared as in Description 3, from 1-(4-hydroxyphenyl)propan-2-one ethylene ketal (3.88 g) as a colourless oil (3.3 g).

$\tau$(CDCl$_3$) 8.0–8.7 (9H, complex), 7.8 (3H, s), 5.9–6.6 (6H, complex), 3.2 (2H, d, J=8 Hz), 2.9 (2H, d, J=8 Hz).

Description 5

1-[4-(11-Hydroxyundecyloxy)phenyl]propan-2-one

The title compound was prepared as in Description 3, from 1-(4-hydroxyphenyl)propan-2-one ethylene ketal (3.88 g) as a colourless oil (6.35 g).

τ(CDCl₃) 8.0–9.1 (19H, complex), 7.75 (3H, s), 5.9–6.5 (6H, complex), 3.2 (2H, d, J=8 Hz), 2.8 (2H, d, J=8 Hz).

Description 6

2-Hydroxy-2-(3-fluoro-4-methoxyphenyl)-ethanamine

To a solution of 3-fluoro-4-methoxybenzaldehyde (5.0 g) in dry ether (100 ml) containing a catalytic amount of zinc iodide was added dropwise a solution of trimethylsilyl cyanide (5 ml) in dry ether. After stirring at room temperature overnight the ether solution was added to an ice-cooled suspension of lithium aluminium hydride (4.0 g) in dry ether (100 ml) under nitrogen. On completion of this addition this mixture was stirred at room temperature for 30 minutes and then boiled under reflux for 1 hour. After boiling in ice this mixture was treated with water (4 ml), 2 N sodium hydroxide solution (4 ml) and water (12 ml) and this resulting suspension was filtered and dried (MgSO₄). Evaporation of the solvent gave a light green oil (3.9 g) which was used without further purification.

τ(CDCl₃) 7.1–7.7 (5H, complex, 3H exchangeable with D₂O), 6.1 (3H, s), 5.3 (1H, complex), 3.1 (3H, complex).

Description 7

4-(2-Hydroxyethoxy)-α,α-dimethylbenzenepropanol

To a suspension of 4-hydroxy-α,α-dimethylbenzenepropanol (15 g, 0.083 m) in water, was added a solution of sodium hydroxide (5 g, 0.125 m) in water (50 ml). 2-Bromoethanol (11.4 g, 0.091 m) and sodium iodide (6.3 g) were successively added and the solution stirred and heated under reflux for 3 hours. The reaction mixture was then diluted with more water and extracted with ethyl acetate. Evaporation of the ethyl acetate gave a cream solid (21.3 g).

τ(CDCl₃) 8.7 (6H, s), 8.0–8.4 (2H, m), 6.9–7.5 (2H, m+2H replaceable by D₂O), 6.0 (4H, bs), 2.7–3.4 (4H, m).

Description 8

3-[4-(2-Hydroxyethoxy)phenyl]-1,1-dimethylpropanamine

To glacial acetic acid (30 ml) at 20° C., was added sodium cyanide (5.3 g) maintaining the temperature of the mixture constant at 20° C. A cooled solution of concentrated sulphuric acid (14.7 ml) and glacial acetic acid (15 ml) was added dropwise with caution. After the initial exothermic reaction, addition proceeded more quickly keeping the temperature approximately 20° C. A solution of 4-(2-hydroxyethoxy)-α,α-dimethylbenzenepropanol (21 g) in glacial acetic acid (75 ml) was added dropwise over 20 minutes and the temperature allowed to rise to ambient. The mixture was stirred for an additional 90 minutes and then allowed to stand overnight. Nitrogen was bubbled through for 20 minutes, the solution poured into water. The desired compound oiled out of solution, the aqueous was decanted and extracted with ethyl acetate. This organic extract was combined with the oily layer, neutralised by sodium carbonate, dried (MgSO₄) and evaporated to give an oil (18 g). The oil (18 g) was mixed with 20% sodium hydroxide (150 ml) stirred vigorously and heated under reflux for 8 hours. After cooling, ethyl acetate was added, the organic layer separated, dried (MgSO₄) and evaporated to give the title compound as an oil which solidified on standing (15 g). The compound was converted to the hydrochloride salt by treatment with an ethereal solution of hydrogen chloride, mp 191°–8° C.

τ(d₆DMSO) 8.6 (6H, s), 7.9–8.3 (2H, m), 7.2–7.6 (2H, m), 6.3 (2H, t, J=5 Hz), 6.15 (2H, t, J=5 Hz), 3.2 (2H, d, J=9 Hz), 2.8 (2H, d, J=9 Hz), 1.6 (bs, 4H, replaceable by D₂O).

Description 9

4-[4-(2-Hydroxyethoxy)phenyl]butan-2-one

A mixture of 4-[4-hydroxyphenyl]butan-2-one (16.4 g], 2-bromoethanol (16.9 g), sodium hydroxide (7.5 g), sodium iodide (7.5 g) and water (200 ml) was heated under reflux for 4 hours, cooled and extracted with dichloromethane. The extract was washed with brine, dried (MgSO₄) and evaporated to dryness. The residual oil was distilled to give the title compound as a colourless liquid, bp 170°–1°/0.8 mm. P τ(CDCl₃) 7.85 (3H, s), 7.15–7.35 (4H, complex), 7.4–7.6 (1H, t), 5.85–6.25 (4H, complex), 2.8–3.4 (4H, dd).

Description 10

N-[2-(4-Carbomethoxymethoxy-3-methylphenyl)-1-methylethyl]-2-hydroxy-2-(3-trifluoromethylphenyl)ethanamine A mixture of 1-(4-carbomethoxymethoxy-3-methylphenyl)propan-2-one (2.15 g) and 2-hydroxy-2-(3-(trifluoromethylphenyl)ethanamine (1.87 g) in benzene (100 ml) was heated under reflux in a Dean and Stark apparatus until water evolution was complete. The solvent was evaporated and the residue dissolved in methanol (50 ml) and hydrogenated at atmospheric pressure over PtO₂. When hydrogen uptake was complete, the catalyst was removed by filtration and the filtrate evaporated to dryness. Chromatography of the residue on silica gel using 4% methanol-dichloromethane gave the title compound as a white solid, mp 75°–9° C. (Et₂O-hexane) as a 57:43 mixture of diastereoisomers.

τ(CDCl₃) 8.95 (3H, d), 7.7 (3H, s), 6.7–7.5 (3H, complex), 6.2 (3H, s), 5.2–5.4 (3H, s on multiplet), 2.8–3.4 (3H, complex, 2.2–2.5 (4H, complex).

Description 11

N-[2-{4-(3-Carbomethoxypropoxy)phenyl}-1-(R)-1-methylethyl]-2-(R)-2-hydroxy-1-oxo-2-(3-trifluoromethylphenyl)-ethanamine

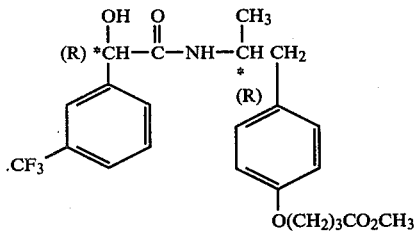

Dicyclohexylcarbodiimide (1.48 g) in DMF (8 ml) was added to a solution of 1-hydroxybenzotriazole (0.97 g), 1-(R)-2-[4-(3-carbomethoxypropoxy)phenyl]-1-methylethanamine (1.54 g) and (R)-3-trifluoromethylmandelic acid (1.57 g) in DMF (30 ml) over 10 minutes at 0° C., with stirring. The mixture was allowed to stand overnight, filtered and evaporated to dryness. The residue was dissolved in ethyl acetate, washed with aqueous sodium carbonate and brine, dried (MgSO₄) and evaporated to dryness. Trituration of the residue with petroleum ether, bp 40°–60°, and filtration gave the title compound, mp 76°–8°, $[\alpha]_{25}^D$ methanol −10.6°, as a white solid of analytical purity.

τ(DMSO-d₆) 9.0 (3H,d), 8.05 (2H, m), 7.2–7.7 (5H, complex), 6.4 (3H,s), 6.1 (2H,t), 5.0 (1H, d. collapsing to s. on D₂O ex), 3.7 (1H,d, exchanged w. D₂O), 2.85–3.3 (4H, dd), 2.0–2.5 (5H, complex; collapsing to 4H on D₂O exchange).

Description 12

1-(R)-2[4-(3-carbomethoxypropoxy)phenyl]-1-methylethanamine hydrochloride

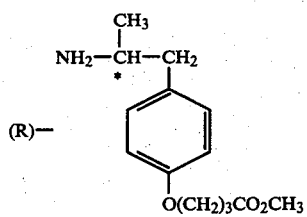

N-[1-(R)-1-phenylethyl]-1-(R)-2-[4-(3-carbomethoxypropoxy-phenyl]-1-methylethanamine hydrochloride (5.6 g) in methanol (40 ml) was hydrogenated in a Parr hydrogenator over 5% Pd/C at 60 psi at 60° for 2 days. The catalyst was removed, the solvent evaporated and the residue crystallised from acetone-ether to give the title compound, mp 134°–6° (acetone-ether), $[\alpha]_D^{25}$ (methanol) −7.9°, as colourless needles of analytical purity.

τ(DMSO-d₆+D₂O) 8.9 (3H,d), 8.0 (2H, m), 6.7–7.7 (5H, complex), 6.4 (3H, s), 6.05 (2H, t), 2.75–3.25 (4H, dd).

Description 13

N-[1-(R)-1-Phenylethyl]-1-(R)-2-[4-(3-carbomethoxypropoxy)-phenyl]-1-methylethanamine hydrochloride

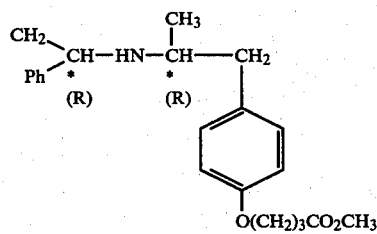

A mixture of 1-(4-(3-carbomethoxypropoxy)phenyl]-propan-2-one (14.8 g) and (+)-α-methylbenzylamine (7.2 g) in dry benzene (90 ml) was heated under reflux under a Dean and Stark apparatus until the theoretical amount of water had been collected. The solvent was evaporated and replaced by ethanol (80 ml). Raney nickel was added and the mixture was hydrogenated in a Parr hydrogenator at ambient temperature under a hydrogen pressure of 60 psi for 6 days. The catalyst was filtered off and the solvent evaporated. The hydrochloride salt was formed by addition of ethereal hydrogen chloride and subsequently recrystallised from acetone-diethyl ether at −60° C. to give the title compound mp 50°–5°, $[\alpha]_{25}^D$ methanol +33.0.

τ(DMSO-d₆+D₂O) 8.9(3H,d), 8.4(3H,d), 7.85–8.2(2H,m), 6.6–7.75(5H, complex), 6.1(2H,t), 5.4(1H,m), 2.9–3.3(4H,dd), 2.2–2.65 (5H, complex), 6.45(3H,s).

CL DEMONSTRATION OF EFFECTIVENESS OF COMPOUNDS

(I) Anti-obesity Activity

The compound of Example 5 was administered by oral gavage in water or carboxymethyl-cellulose suspension to genetically obese mice daily for 28 days. At the end of the time the carcass composition was determined. The result obtained was as follows:

| COMPOUND OF EXAMPLE NO. | DOSE mg/kg p.o. | g LIPID/MOUSE TREATED | CONTROL |
|---|---|---|---|
| 5 | 12.2 | 15.80 | 18.75 |

(II) Effect on Energy Expenditure

The effect of the compounds of the Examples on the energy expenditure of mice was demonstrated by means of the following procedure.

Female CFLP mice each weighing approximately 24 g were given food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content following the principles described by J. B. de V. Weir, J. Physiol. (London) 109, 1–9 (1949). The food intake of the mice was measured over this same period of 21 hours. The results are expressed as a percentage of the mean food intake or rate of energy expenditure of the mice dosed with water.

| COMPOUND OF EXAMPLE NO. | DOSE mg/kg po | MEAN ENERGY EXPENDITURE (%) | | MEAN FOOD INTAKE (%) |
|---|---|---|---|---|
| | | 0–3h | 0–21h | |
| 1 | 18.5 | 176 | 128 | 70 |
| 2 | 22.9 | 168 | 135 | 89 |
| 3 | 20.0 | 178 | 134 | 82 |
| 4 | 22.2 | 179 | 121 | 75 |
| 5 | 24.5 | 213 | 129 | 103 |
| 6 | 23.3 | 132 | 101 | 99 |
| 7 | 24.9 | 145 | 118 | 116 |
| 8 | 20.2 | 138 | 96 | 86 |
| 9 | 19.1 | 102 | 98 | 91 |
| 10 | 20.3 | 159 | 114 | 88 |
| 11 | 22.1 | 136 | 113 | 115 |
| 13 | 5.7 | 134 | 116 | 93 |

(III) Cardiac Activity

Rat hearts were perfused by the Langendorff procedure.

Hearts were dissected free within 30 seconds of death and reverse perfused via the aorta and coronary vessels with Krebs-Ringer bicarbonate solution (pH 7.4, 37° C.) gassed with 95% oxygen: 5% carbon dioxide at a flow rate between 8–12 cm³/minute. Responses were observed after injection of drug dissolved in isotonic saline into the perfusion media. Heart rate and tension were displayed on an Ormed MX2P recorder via a tension transducer and heart ratemeter.

Results are expressed as a percentage of the maximum response due to salbutamol.

| COMPOUND OF EXAMPLE NO. | DOSE ADDED TO PERFUSATE (μg) | HEART TENSION | HEART RATE |
|---|---|---|---|
| Salbutamol | — | 100 | 100 |
| 1 | 30 | 53 | 63 |
| 2 | 30 | 22 | 0 |
| 3 | 30 | 50 | 17 |
| 4 | 30 | 0 | 7 |
| 5 | 30 | 0 | 0 |
| 6 | 30 | 36 | 0 |
| 7 | 30 | 29 | 46 |
| 8 | 30 | 13 | 13 |
| 13 | 30 | 47 | 17 |

(IV) Hypoglycaemic Activity

Female CFLP mice, weighing approximately 25 g, were fasted for 24 hours prior to the study. The compounds under study were administered orally as an aqueous solution to each of 8 mice. 30 minutes later a blood sample (20 μm$^3$) was obtained from the tail for the analysis of blood glucose. Immediately after taking this blood sample, glucose (1 g/kg body weight) was administered subcutaneously to each mouse. 8 mice were given water as a control. Blood samples were then obtained from each mouse at 30 minute intervals for 120 minutes.

Compounds that produced a significant (P<0.05) reduction on blood glucose, compared with control mice given water, at any time interval, were considered active. The area under the blood glucose curve over the 2 hour period after the administration of the glucose was calculated for each compound and compared with the value for control animals.

| COMPOUND OF EXAMPLE NO. | DOSE (μmol/kg) | REDUCTION IN AREA UNDER BLOOD GLUCOSE CURVE (%) |
|---|---|---|
| 1 | 3.0 | 61 |
| 2 | 2.4 | 57 |
| 3 | 2.5 | 52 |
| 4 | 1.0 | 31 |
| 5 | 1.0 | 59 |
| 6 | 2.5 | 24 |
| 7 | 2.5 | 45 |
| 8 | 12.5 | 21 |
| 9 | 50.0 | 55 |
| 10 | 2.5 | 23 |
| 11 | 1.0 | 31 |
| 13 | 1.0 | 37 |

(V) Anti-inflammatory Activity

The method used is based on that described by G. Tonelli et al (Endocrinology, 77, 625–634, 1965). An inflammation is induced in the rat ear by the application of 50 μl of a 1% solution of croton oil in tetrahydrofuran, test compounds being dissolved in the irritant vehicle. After 6 hours the inflammation is assessed by killing the animals and weighing the ears. Topical anti-inflammatory activity of a compound is generally considered to be shown when a significant (5% level) reduction in ear weight is seen compared to non-drug treated control.

| COMPOUND OF EXAMPLE NO. | DOSE mg/rat ear | ACTIVITY |
|---|---|---|
| 1 | 2 | Active |
| 1 | 0.5 | Slightly active |
| 4 | 0.5 | Active |

(VI) Platelet Aggregation Inhibition Activity

Male CFLP mice (ca 20 g, n=8) were dosed orally with compound or vehicle (controls) after an overnight fast. Two hours later each mouse received an intravenous dose of collagen (400 μg/kg, pH 6–6.6). Exactly 30 sec. after injection of collagen, each mouse was placed in a chamber of $CO_2$ until respiration ceased. Blood platelet concentration was determined (Ultra-Flo 100 whole blood platelet counter, Clay Adams) in blood samples (3 μl) taken immediately from the inferior vena cava. Each concentration was expressed as a percent of that obtained in a tail blood sample taken immediately before injection of collagen. Results are given in the table below.

| COMPOUND OF EXAMPLE NO. | DOSE po μmol/kg | % INHIBITION OF RESPONSE TO COLLAGEN |
|---|---|---|
| Aspirin | 600 | 47 |
| 2 | 1 | 26 |
| 3 | 1 | 47 |
| 5 | 1 | 47 |

I claim:

1. A compound of formula (I):

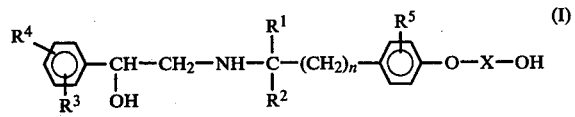

or a salt thereof; wherein $R^1$ is hydrogen, methyl or ethyl; $R^2$ is hydrogen, methyl or ethyl; $R^3$ is hydrogen, fluorine, chlorine, bromine or trifluoromethyl; each of $R^4$ and $R^5$ is hydrogen, fluorine, chlorine, bromine, $C_{1-6}$ alkyl or $C_{1-6}$ alkoxy; n is 1 or 2; and X is $C_{1-12}$ straight or branched alkylene.

2. A compound according to claim 1, wherein each of $R^4$ and $R^5$ is hydrogen, and X is $C_{1-6}$ straight or branched alkylene.

3. A compound according to claim 1, wherein n is 1.

4. A compound according to claim 1, selected from N-[2-(4-(2-hydroxyethoxy)phenyl)-1-methylethyl]-2-hydroxy-2-(2-fluoro-phenyl)ethanamine; N-[2-(4-(4-hydroxybutoxy) phenyl)-1-methylethyl]-2-hydroxy-2-(3-trifluoromethylphenyl)ethanamine; N-[2-(4-(2-hydroxyethoxy)phenyl)-1-methylethyl]-2-hydroxy-2-(3-trifluoromethylphenyl) ethanamine; N-[2-(4-(3-hydroxypropyloxy)phenyl)-1-methylethyl]-2-hydroxy-2-(3-trifluoromethylphenyl)ethanamine; N-[2-(4-(6-hydroxyhexyloxy)phenyl)-1-methylethyl]-2-hydroxy-2-(3-trifluoromethylphenyl)ethanamine; N-[2-(4-(11-hydroxyundecyloxy)phenyl)-1-methylethyl]-2-hydroxy-2-(3-trifluoromethylphenyl)ethanamine; N-[2-(4-(1,1-dimethyl-2-hydroxyethoxy)phenyl)-1-methylethyl]-2-hydroxy-2-(3-trifluoromethylphenyl)ethanamine; N-[2-(4-(2-hydroxyethoxy)phenyl)-1-methylethyl]-2-hydroxy-2-(3-fluoro-4-methoxyphenyl)ethanamine; N-[3-[4-(2-hydroxyethoxy)phenyl]-1,1-dimethylpropyl]-2-hydroxy-2-phenylethanamine; N-[3-(4-(2-hydroxyethoxy)phenyl)-1-methylpropyl]-2-hydroxy-2-

(3-chlorophenyl)ethanamine; N-[2-{4-hydroxyethoxy)-3-methylphenyl}-1-methylethyl]-2-hydroxy-2-(3-trifluoromethylphenyl)ethanamine; N-[2-(4-(2-hydroxyethoxy)-phenyl)-1-methylethyl]-2-hydroxy-2-(3-chlorophenyl)ethanamine and salts thereof.

5. A pharmaceutical composition useful in the treatment of obesity or hypoglycaemia, comprising an effective amount of a compound of formula (I) as defined in claim 1, or a pharmaceutically acceptable salt thereof, in combination with a pharmaceutically acceptable carrier therefor.

6. A composition according to claim 5 in unit dose form, comprising from 0.1 to 500 mg of the compound of formula (I) or a salt thereof, per unit dose.

7. A method for treating obesity in human or non-human animals comprising administering an effective, non-toxic amount of a compound of formula (I) or a pharmaceutically acceptable salt thereof, as defined in claim 1, to an obese animal.

8. A method of treating hyperglycaemia in human or non-human animals comprising administering an effective, non-toxic amount of a compound of formula (I) or a pharmaceutically acceptable salt, thereof as defined in claim 1 to a hyperglycaemic animal.

* * * * *